United States Patent
Clasbrummel et al.

(10) Patent No.: US 9,161,795 B2
(45) Date of Patent: Oct. 20, 2015

(54) BONE PLATE SYSTEM FOR OSTEOSYNTHESIS

(75) Inventors: Bernhard Clasbrummel, Balingen (DE); Curt Kranz, Berlin (DE); Susanne Kahl, legal representative, Berlin (DE)

(73) Assignee: Merete Medical GmbH, Berlin (DE)

( * ) Notice: Subject to any disclaimer, the term of this patent is extended or adjusted under 35 U.S.C. 154(b) by 389 days.

(21) Appl. No.: 13/517,949

(22) PCT Filed: Dec. 21, 2010

(86) PCT No.: PCT/DE2010/075167
§ 371 (c)(1),
(2), (4) Date: Jan. 3, 2013

(87) PCT Pub. No.: WO2011/076205
PCT Pub. Date: Jun. 30, 2011

(65) Prior Publication Data
US 2013/0165981 A1    Jun. 27, 2013

(30) Foreign Application Priority Data

Dec. 22, 2009 (DE) .......................... 10 2009 060 396
Apr. 20, 2010 (DE) .......................... 20 2010 005 260

(51) Int. Cl.
*A61B 17/80* (2006.01)
*A61B 17/86* (2006.01)

(52) U.S. Cl.
CPC ........... *A61B 17/863* (2013.01); *A61B 17/8033* (2013.01); *A61B 17/8038* (2013.01); *A61B 17/8042* (2013.01); *A61B 17/8057* (2013.01); *A61B 17/8605* (2013.01)

(58) Field of Classification Search
CPC .... A61B 17/58; A61B 17/7059; A61B 17/80; A61B 17/8014; A61B 17/8052
USPC .......... 606/280, 283, 284, 286, 287, 289, 291
See application file for complete search history.

(56) References Cited

U.S. PATENT DOCUMENTS

| 2,662,988 A | 12/1935 | McKim |
| 3,741,205 A | 6/1973 | Markolf et al. |

(Continued)

FOREIGN PATENT DOCUMENTS

| AT | 406 446 B | 5/2000 |
| DE | 3113639 | 5/1982 |

(Continued)

OTHER PUBLICATIONS

International Search Report for parent application PCT/DE2010/075167, having a mailing date of Apr. 15, 2011.

(Continued)

*Primary Examiner* — Anu Ramana
(74) *Attorney, Agent, or Firm* — Andrus Intellectual Property Law, LLP

(57) ABSTRACT

A bone plate system for osteosynthesis comprises a bone plate, a swivel screw, a clamping screw, a swivel hole formed in the bone plate as a through hole for receiving the swivel screw polyaxially, and a clamping hole, which is associated with the swivel hole and is formed in the bone plate as a further through hole for receiving the clamping screw. When the swivel screw and the clamping screw are screwed in, they are fixed with angular stability in multiple dimensions, as the screw heads of the swivel screw and of the clamping screw are secured by one another and by the bone plate against relative movement. The swivel screw and the clamping screw are each designed as a bone screw.

18 Claims, 12 Drawing Sheets

(56) References Cited

U.S. PATENT DOCUMENTS

| | | | |
|---|---|---|---|
| 3,757,591 | A | 9/1973 | Taylor |
| 4,408,601 | A | 10/1983 | Wenk |
| 4,454,876 | A | 6/1984 | Mears |
| 4,616,634 | A | 10/1986 | Vargas Garcia |
| 4,720,225 | A | 1/1988 | Burt |
| 4,903,691 | A | 2/1990 | Heinl |
| 4,959,065 | A | 9/1990 | Arnett et al. |
| 5,529,075 | A | 6/1996 | Clark |
| 5,709,686 | A | 1/1998 | Talos et al. |
| 6,129,728 | A | 10/2000 | Schumacher et al. |
| 6,152,927 | A * | 11/2000 | Farris et al. .......... 606/287 |
| 6,203,545 | B1 | 3/2001 | Stoffella |
| 6,206,883 | B1 | 3/2001 | Tunc |
| 6,293,949 | B1 * | 9/2001 | Justis et al. .......... 606/279 |
| 6,306,140 | B1 | 10/2001 | Siddiqui |
| 6,398,783 | B1 | 6/2002 | Michelson |
| 6,423,068 | B1 | 7/2002 | Reisberg et al. |
| 6,669,701 | B2 | 12/2003 | Steiner et al. |
| 6,716,957 | B2 | 4/2004 | Tunc |
| 6,719,759 | B2 | 4/2004 | Wagner et al. |
| 6,730,091 | B1 | 5/2004 | Pfefferle et al. |
| 6,886,799 | B2 | 5/2005 | Yamanashi |
| 7,008,428 | B2 | 3/2006 | Cachia et al. |
| 7,354,441 | B2 | 4/2008 | Frigg |
| 7,468,069 | B2 | 12/2008 | Baynham et al. |
| 7,655,029 | B2 | 2/2010 | Niederberger et al. |
| 7,771,457 | B2 | 8/2010 | Kay et al. |
| 7,976,570 | B2 | 7/2011 | Wagner et al. |
| 8,118,848 | B2 | 2/2012 | Ducharme et al. |
| 8,246,661 | B2 | 8/2012 | Beutter et al. |
| 8,632,545 | B2 | 1/2014 | Sarangapani et al. |
| 2002/0045897 | A1 | 4/2002 | Dixon et al. |
| 2002/0045901 | A1 | 4/2002 | Wagner et al. |
| 2002/0183752 | A1 | 12/2002 | Steiner et al. |
| 2003/0078668 | A1 | 4/2003 | Michelson |
| 2004/0018228 | A1 | 1/2004 | Fischell et al. |
| 2004/0034356 | A1 | 2/2004 | LeHuec et al. |
| 2004/0073218 | A1 | 4/2004 | Dahners |
| 2004/0102778 | A1 | 5/2004 | Huebner et al. |
| 2004/0167522 | A1 | 8/2004 | Niederberger et al. |
| 2004/0215192 | A1 | 10/2004 | Justis et al. |
| 2004/0236332 | A1 | 11/2004 | Frigg |
| 2005/0015092 | A1 | 1/2005 | Rathbun et al. |
| 2005/0049594 | A1 | 3/2005 | Wack et al. |
| 2005/0065521 | A1 | 3/2005 | Steger et al. |
| 2005/0085818 | A1 | 4/2005 | Huebner |
| 2005/0124994 | A1 | 6/2005 | Berger et al. |
| 2005/0165400 | A1 | 7/2005 | Fernandez |
| 2005/0165401 | A1 | 7/2005 | Pack |
| 2005/0182408 | A1 | 8/2005 | Pfefferle et al. |
| 2005/0192577 | A1 | 9/2005 | Mosca et al. |
| 2005/0261688 | A1 | 11/2005 | Grady, Jr. et al. |
| 2006/0015102 | A1 | 1/2006 | Toullec et al. |
| 2006/0173458 | A1 | 8/2006 | Forstein et al. |
| 2006/0235396 | A1 | 10/2006 | Sanders et al. |
| 2006/0241607 | A1 | 10/2006 | Myerson et al. |
| 2007/0016205 | A1 | 1/2007 | Beutter et al. |
| 2007/0123885 | A1 | 5/2007 | Kirschman |
| 2007/0233106 | A1 | 10/2007 | Horan et al. |
| 2007/0276386 | A1 | 11/2007 | Gerlach et al. |
| 2008/0051786 | A1 | 2/2008 | Jensen |
| 2008/0132955 | A1 | 6/2008 | Frigg |
| 2008/0300637 | A1 | 12/2008 | Austin et al. |
| 2009/0024172 | A1 | 1/2009 | Pizzicara |
| 2009/0210010 | A1 | 8/2009 | Strnad et al. |
| 2010/0256687 | A1 | 10/2010 | Neufeld et al. |
| 2011/0264149 | A1 | 10/2011 | Pappalardo et al. |
| 2011/0295325 | A1 | 12/2011 | Wagner et al. |
| 2012/0265254 | A1 | 10/2012 | Horan et al. |
| 2013/0190829 | A1 | 7/2013 | Batsch et al. |

FOREIGN PATENT DOCUMENTS

| | | |
|---|---|---|
| DE | 10 2005 044 841 A1 | 3/2006 |
| DE | 10 2006 000 948 A1 | 10/2006 |
| DE | 10 2005 043 285 B3 | 1/2007 |
| DE | 698 35 968 T2 | 5/2007 |
| DE | 102007005417 | 6/2008 |
| DE | 10 2005 042 766 B4 | 8/2009 |
| DE | 102010025001 | 12/2011 |
| EP | 0243114 | 10/1987 |
| EP | 0243114 | 11/1990 |
| EP | 1255498 | 11/2002 |
| EP | 1158916 | 7/2004 |
| EP | 1158915 | 9/2004 |
| EP | 1468655 | 10/2004 |
| EP | 1255498 | 11/2005 |
| EP | 1677693 | 7/2006 |
| EP | 1 702 577 A2 | 9/2006 |
| EP | 1897509 | 3/2008 |
| EP | 1468655 | 5/2008 |
| EP | 2016918 | 1/2009 |
| EP | 1677693 | 4/2009 |
| FR | 2667913 | 4/1992 |
| FR | 2739151 | 3/1997 |
| FR | 2 886 535 A1 | 12/2006 |
| WO | 9709000 | 3/1997 |
| WO | 9829058 | 7/1998 |
| WO | 0053110 | 9/2000 |
| WO | 0154601 | 8/2001 |
| WO | 02096309 | 12/2002 |
| WO | 2005/041769 A1 | 5/2005 |
| WO | 2005041796 | 5/2005 |
| WO | 2005053111 | 6/2005 |
| WO | 2006/014436 A1 | 2/2006 |
| WO | 2007/025520 A1 | 3/2007 |
| WO | 2009058969 | 5/2009 |
| WO | 0053110 | 9/2009 |
| WO | 2010059497 | 5/2010 |
| WO | 2010115403 | 10/2010 |
| WO | 2011076205 | 6/2011 |
| WO | 2011163092 | 12/2011 |
| WO | 2012000627 | 1/2012 |
| WO | 2012/000627 | 5/2012 |

OTHER PUBLICATIONS

International Search Report and Written Opinion for PCT/DE2013/100117, mailed Jul. 18, 2013.

Sammarco, V. James; Surgical Strategies: Mau Osteotomy for Correction of Moderate and Severe Hallux Valgus Deformity; Foot & Ankle International; Jul. 2007; 28(7); pp. 857-864.

International Search Report for PCT/DE2010/000365, mailed Sep. 8, 2010.

International Search Report for PCT/DE2012/100248 dated Dec. 20, 2012.

Partial International Search Report for PCT/IB2014/001111 dated Sep. 16, 2014.

Easley, Mark E., M.D., et al., Current Concepts Review: Hallux Valgus Part II: Operative Treatment, Foot & Ankle International, vol. 28/ No. 6, 748-758 (Jun. 2007).

Iselin, Lukas D. et al., Operative Management of Common Forefoot Deformities A Representative Survey of Australian Orthopaedic Surgeons, Foot & Ankle Specialist, vol. X/ No. X, 1-7 (2012).

Miller, Michael J., DMP et al., Inverted Z-scarf Osteotomy for Hallux Valgus Deformity Correction: Intermediate-term Results in 55 Patients, The Journal of Foot and Ankle Surgery, 50: 55-61 (2011).

Dereymaeker, Greta, MD, PhD, Scarf Osteotomy for Correction of Hallux Valgus—Surgical Technique and Results as Compared to Distal Cheveron Osteotomy, The Hallux, vol. 5/ No. 3, 513-523 (Sep. 2000).

Steck, Jerome K., DPM, Long Z-Osteotomy: A Review and New Modification to Correct Troughing, The Journal of Foot and Ankle Surgery, vol. 40/ No. 5, 305-310 (Sep./Oct. 2001).

Adam, Stephanie P., DO et al., Outcomes after Scarf Osteotomy for Treatment of Adult Hallux Valgus Deformity, Clinical Orthopaedics and Related Research, 469: 854-859 (2011).

(56) References Cited

OTHER PUBLICATIONS

Trnka, Hans-Jorg, MD et al., Six First Metatarsal Shaft Osteotomies—Mechanical and Immobilization Comparisons, Clinical Orthopaedics and Related Research, No. 381, 256-265 (Mar. 10, 2000).
Aminian, Arash, M.D. et al., Scarf Osteotomy for Hallux Valgus Deformity: An Intermediate Followup of Clinical and Radiographic Outcomes, Foot & Ankle International, vol. 27/ No. 11, 883-886 (Nov. 2006).
Weil, Lowell Scott, DPM, Scarf Osteotomy for Correction of Hallux Valgus—Historical Perspective, Surgical Technique, and Results, The Hallux, vol. 5/ No. 3, 559-580 (Sep. 2000).
Vienne, Patrick, M.D. et al, Comparative Mechanical Testing of Different Geometric Designs of Distal First Metatarsal Osteotomies, Foot & Ankle International, vol. 28/ No. 2, 232-236 (Feb. 2007).
Lipscombe, Stephen, MRCS et al, Scarf Osteotomy for the Correction of Hallux Valugs: Midterm Clinical Outcome, The Journal of Food and Ankle Surgery, vol. 47/ No. 4, 273-277 ( Jul./Aug. 2008).
Barouk, Louis Samuel, MD, Scarf Osteotomy for Hallux Valgus Correction—Local Anatomy, Surgical Technique, and Combination with Other Forefoot Procedures, The Hallux, vol. 5/ No. 3, 525-557 (Sep. 2000).
Crevoisier, Xavier et al., The Scarf Osteotomy for the Treatment of Hallux Valgus Deformity: A Review of 84 Cases, Foot & Ankle International, vol. 22/ No. 12, 970-976 (Dec. 2001).
Coetzee, J. Chris, M.D., Scarf Osteotomy for Hallux Valgus Repair: The Dark Side, Foot & Ankle International, vol. 24/ No. 1, 29-33 (Jan. 2003).
Interventional Procedures Programme—Interventional procedure overview of surgical correction of hallux valgus using minimal access techniques, National Institute for Health and Clinical Excellence, p. 1, 9.
Comparison of Preoperative to Postoperative Measurement at 6 Weeks, 1 and 2 Years Postoperative, Table 1.
O'Briain, David E. et al., Use of A Geometric Formula to Improve the Radiographic Correction Achieved by the Scarf Osteotomy, Foot & Ankle International, vol. 33/ No. 8, 647-654 (Aug. 2012).
Acevedo, Jorge I, Sammarco, V. James, Boucher, Henry R., Parks, Bert G., Schon, Lew C., Myerson, Mark S; Mechanical Comparison of Cyclic Loading in Five Different First Metatarsal Shaft Osteotomies; Foot & Ankle International, Aug. 2002; vol. 23, No. 8, pp. 711-716.
Cisar, J., Holz, U, Jenninger, w., Uhlig. Chr.; Die Osteotomie nach Ludloff bei der Hallux-valgus-Operation; Aktuelle Traumatol. 13; 1983; pp. 247-249.
Hyer, Christopher F., Glover, Jason P., Berlet, Gregory C., Philbin, Terrence, M, Lee, Thomas H.; A Comparison of the Crescentic and Mau Osteotomies for Correction of Hallux Valgus; Journal of Foot and Ankle Surgery; Mar./Apr. 2008; vol. 47, No. 2,; pp. 103-111.
Ludloff, Prof. Dr. K.; Die Beseitigung des Hallux valgus durch die schrage planta-dorsale Osteotomie des Metatarus I.; Arch. Klin. Chir.; 110:364-387; 1918.
Mau, C., Lauber, H.J.; Die operative Behandlung des Hallux valgus (Nachuntersuchungen); 1926, 197:361-377.
Sammarco, V. James; Surgical Strategies: Mau Osteotomy for Correction of Moderate and Severe Hallux Valgus Deformity; Foot 8 Ankle International; Jul. 2007; 28(7); pp. 857-864.
Saxena, Amol, McCammon, Derek; The Ludloff Osteotomy: A Critical Analysis; Journal of Foot and Ankle Surgery; 1997; vol. 36, No. 2, pp. 100-105.
Trnka, H.-J., Hofstaetter, S.G., Hofstaetter, J.G., Gruber, F., Adams Jr., S.B., Easley, M.E.; Intermediate-Term Results of the Ludloff Osteotomy in One Hundred and Eleven Feet; The Journal of Bone and Joint Surgery; Mar. 2008; vol. 90-A(3); pp. 531-539.
International Search Report for PCT/2006/001508, mailed Feb. 8, 2007.
"Orthopaedic Product News", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate.

* cited by examiner

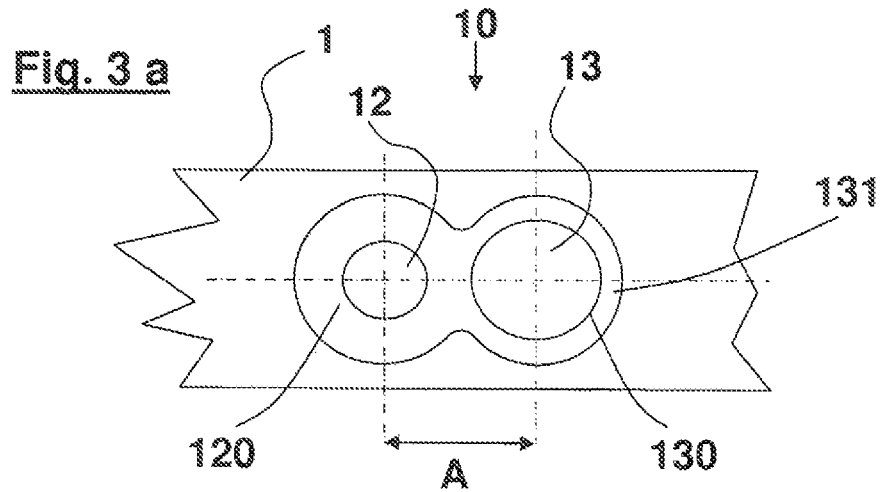
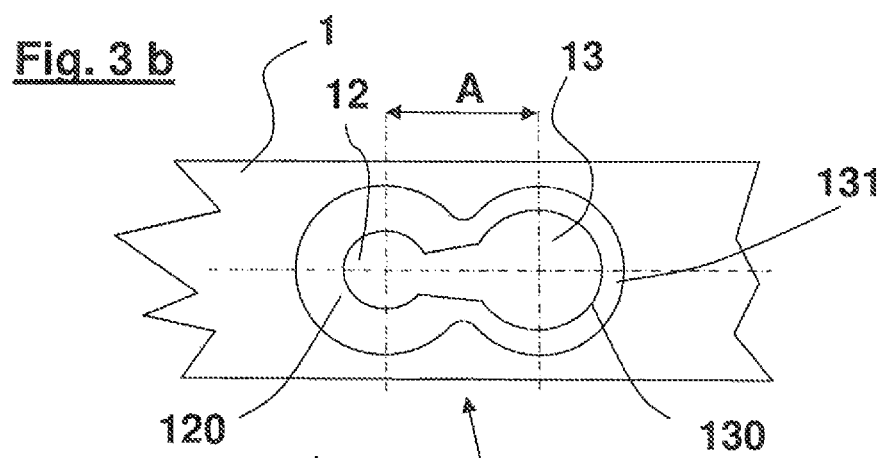
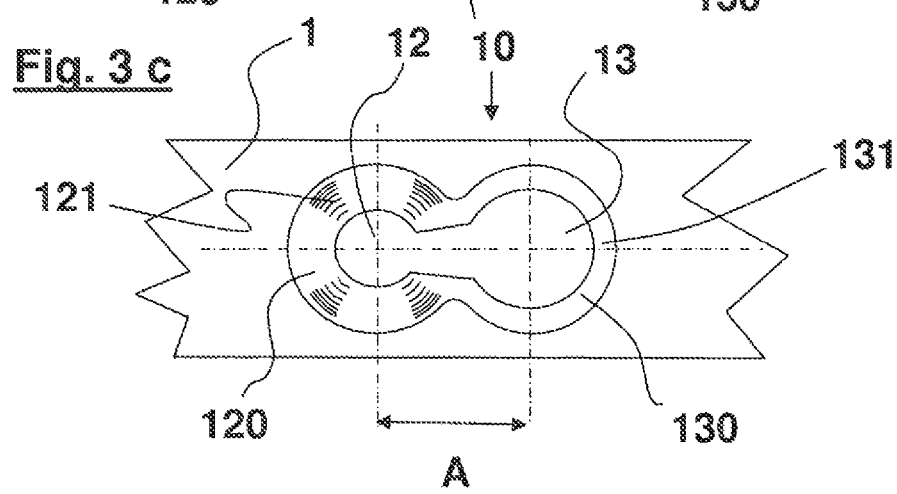

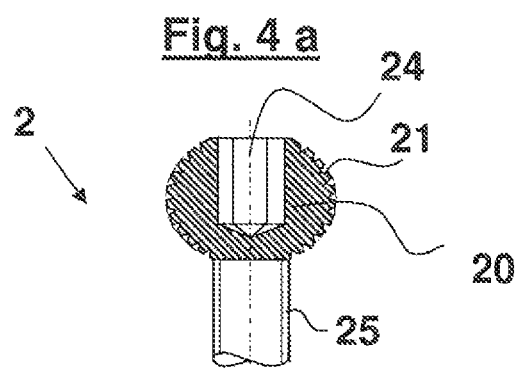
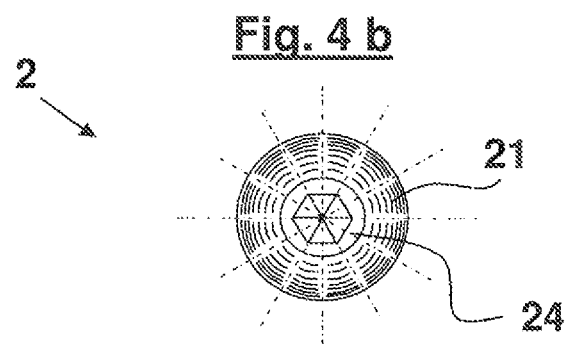

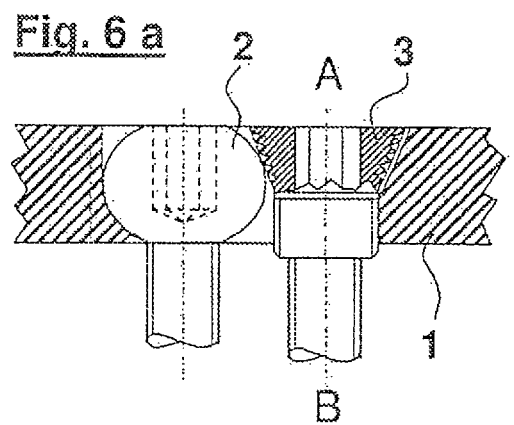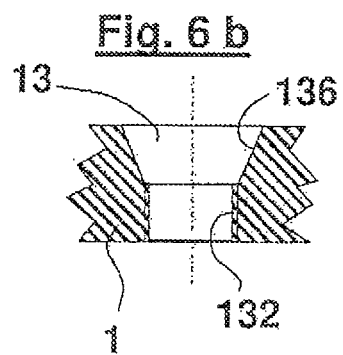

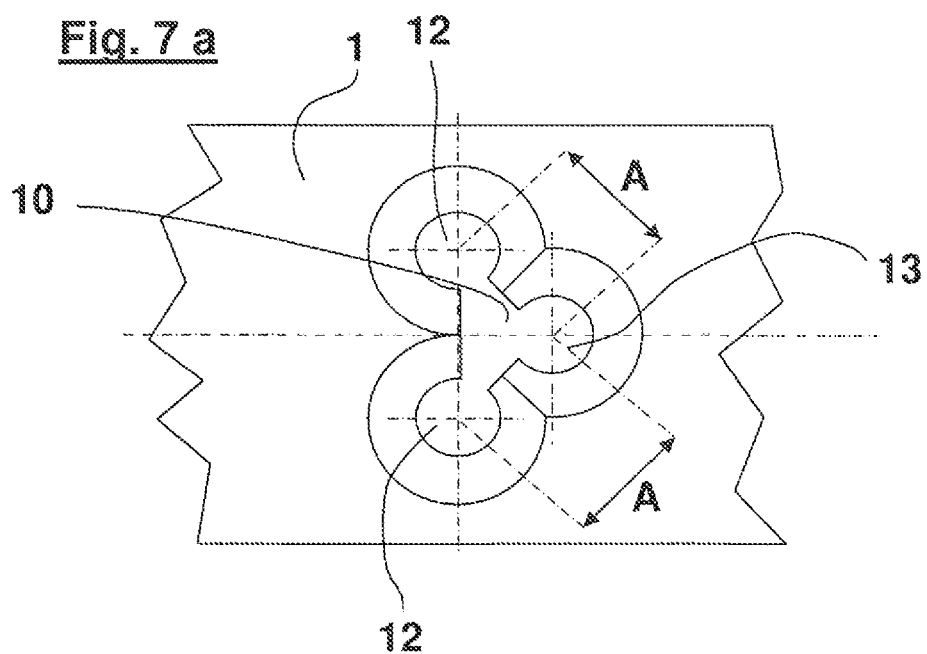
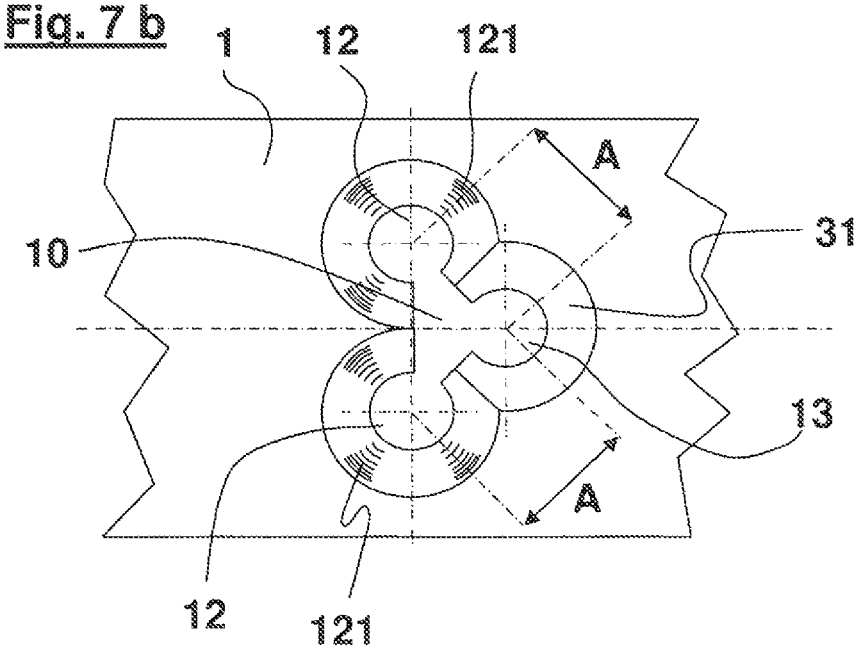

BONE PLATE SYSTEM FOR OSTEOSYNTHESIS

CROSS-REFERENCE TO RELATED APPLICATIONS

This application is the U.S. national stage application of International Application No. PCT/DE2010/075167, filed Dec. 21, 2010, which International application was published on Jun. 30, 2011 as International Publication No. WO 2011/076205 A1 in the German language and which application is incorporated herein by reference. The International application claims priority of German Patent Application No. 10 2009 060 396.4, filed Dec. 22, 2009, and German Patent Application No. 20 2010 005 260.2, filed Apr. 20, 2010, which applications are incorporated herein by reference.

The invention relates to technologies in the field of bone plate systems for osteosynthesis.

BACKGROUND OF THE INVENTION

Bone plate systems provide fixed-angle fixation of a bone plate by means of assigned screws for osteosynthesis in the human or animal body. Numerous bone plate systems are known that generally include a bone plate with an arrangement of a plurality of through-holes and associated screws. In addition to so-called bone screws, that is, screws that are screwed into the bone during fixation, fastening screws may be provided that are themselves not screwed into the bone but rather are screwed into a thread formed in the bone plate. Such fastening screws are then used for instance for fixing the bone screws (see for instance documents EP 1 702 577 A2, WO 2006/014436 A1, and AT 406 446 B). A fastening screw for fixing a plurality of bone screws is also used in the system for cervical vertebra in document DE 698 35 968 T2.

Document WO 2005/041769 A1 discloses a bone plate that is provided with longitudinal holes.

Fixed-angle plate-screw connections to osteosynthesis plates have the advantage of better anchoring of the bone plate to the bone. This is particularly advantageous with bone fractures close to a joint, since in this manner it is possible to better capture and fix bone fragments that are close to a joint. The advantage of fixed-angle plate-screw connections is even more significant in osteoporotic bone fractures close to a joint, since non-fixed-angle bone screws are not able to fix an osteoporotic bone as well.

Fixed-angle plate-screw connections can be divided into monoaxial and polyaxial plate-screw connections.

Examples of monoaxial fixed-angle plate-screw connections are presented in documents DE 10 2005 044 841 B4 and DE 10 2005 043 285 B3. These systems are characterized in that they have screw heads with male threads that engage in corresponding female threads of plates. If a screw is screwed in during an operation, the positive fit between the male thread of the screw head and the female thread of the bone plate effects a fixed-angle plate-screw connection during the last rotations of the screwing-in process.

Furthermore, bone plate systems have been suggested in which bone screws are variable with respect to their swivel or angular position relative to the bone plate during use. Such a bone plate system is described for instance in document DE 10 2006 000 948 A1. Document WO 2007/025520 A1 discloses a bone plate having at least one screw for fixed-angle fixation. Another example of a polyaxial fixed-angle plate-screw connection is disclosed in DE 10 2005 042 766 B4. The embodiment of a female thread from six female thread columns makes it possible to screw in spherical head screws having a special male thread in the polyaxial direction and to fix them in a fixed-angle manner during the last rotations of the screwing-in process. Such plate-screw systems have become increasingly common in clinical practice due to clinical advantages of a polyaxial fixed-angle fixation option.

A disadvantage of known fixed-angle bone plate systems is the lack of an option for drawing bone fragments to the bone plate during the process of tightening, since, due to its thread on the screw head, the thread of the screw head locks up in the bone plate during the last rotation. However, near a joint it is often necessary to draw in fragments in order to attain better restoration of the original anatomy. Moreover, for weakened osteoporotic bones there is a lack of plate systems with options for fixing a plurality of screws to or in a bone plate at a fixed angle in a narrow space.

SUMMARY OF THE INVENTION

The object of the invention is to provide new technologies in the field of bone plate systems for osteosynthesis, which bone plate systems can be flexibly employed by the user and have enhanced practicality in use and optimized angular stability for the bone screws.

This object is inventively attained using a bone plate system for osteosynthesis according to independent claim 1. Advantageous embodiments of the invention are the subject-matter of dependent subordinate claims.

The invention encompasses the thought of a bone plate system for osteosynthesis having a bone plate, a swivel screw, a clamping screw, a swivel hole that is formed in the bone plate as a through-hole for polyaxially receiving the swivel screw, and a clamping hole that is associated with the swivel hole and that is formed in the bone plate as an additional through-hole for receiving the clamping screw, wherein when screwed in the swivel screw and the clamping screw are fixed multidimensionally at a fixed angle in that screw heads of the swivel screw and the clamping screw are secured to one another and to the bone plate against a relative movement, and wherein the swivel screw and the clamping screw are each embodied as bone screws.

In the suggested bone plate system, bone screws, that is, the swivel screw that is adjustable relative to its swivel position to the bone plate and the clamping screw that is essentially fixed with respect to its relative position to the bone plate, which clamping screw can also be called the fixation or fixing screw, are multiply stabilized with respect to their spatial angular position relative to one another and to the bone plate when screwed in in that the screw heads of the two screws are secured to one another and the screw heads are secured to the edge areas of the through-holes in the bone plate and thus are secured to the bone plate itself against relative movement. This securing against relative movement preferably occurs by means of a friction or positive fit, for instance by locking up. The screwed-in condition means that both swivel screw and also clamping screw are screwed into the bone, since both screws are embodied as bone screws, which is reflected especially by a corresponding bone thread on each screw shaft.

In one embodiment, the additional through-hole is for monoaxially receiving the clamping screw.

In one embodiment, the swivel screw and/or the clamping screw may have a polygonal recess or a star-shaped recess in the screw head. Other screw profiles such as for instance Phillips, Pozidriv, Torx, square, tri-wing, Torq-set, or spanner may be used.

The elements of the bone plate system, that is especially the bone plate and/or the swivel screw and/or the clamping screw, are preferably made of a titanium alloy.

The mutual support of locking up of the screw heads with one another and with the bone plate itself makes it possible to do without an additional system for fixing the bone screws to the bone plate, as this is provided in known systems in the prior art.

One preferred refinement of the invention provides that the swivel hole is formed with a spherical head seat opening to the top of the bone plate and the swivel screw has an associated spherical head that, when the swivel screw is screwed in, is arranged at least in part in the spherical head seat of the swivel hole.

In one useful embodiment of the invention it can be provided that the spherical head seat is formed at least in segments with an essentially smooth surface and/or at least in segments with a surface contour. Smooth surface segments have the advantage that the swivel positions of the swivel screw in the swivel hole can be selected closely stepped within structurally imposed limits. Surface contours in the area of the spherical head seat can provide additional support to angular stability in the swivel position used by the swivel screw.

One refinement of the invention usefully provides that the clamping hole has a female thread. The female thread is completely formed in a segment of the clamping whole or in the clamping hole. In this manner the clamping hole is embodied as a screw hole. The female thread may be a sharp V female thread. The clamping hole may be entirely or partly cylindrical so that at least a cylindrical thread section is produced. A conical segment may also be provided in the clamping hole, preferably on a side of the bone plate that faces away from the bone. In this manner it is possible to form a conical thread segment. If the clamping screw has a countersunk head, in one embodiment the latter is entirely or partly received in a positive fit in the conical segment.

One preferred refinement of the invention provides that the screw head of the clamping screw has a male thread. The male thread is formed corresponding to the female thread of the clamping hole so that the male thread screws into the female thread, at least in part, when the clamping screw is screwed in.

A further embodiment of the invention can provide that the screw head of the swivel screw has a thread contour that is formed with essentially horizontal circumferential grooves and with a right-handed thread as well as a left-handed thread, the male thread of the screw head for the clamping screw when the clamping screw is screwed in is at least partially screwed into the female thread of the clamping hole and when screwed in surface segments of the thread contour on the screw head of the swivel screw and of the male thread on the screw head of the clamping screw mutually engaging in a positive fit. The angular stability is especially supported in that thread segments of the two screw heads mutually engage in a positive fit at least when completely screwed in. The thread contour on the spherical head of the swivel screw, which is formed with circumferential surface grooves as well as right-handed and left-handed threads make it possible for the thread contour to engage in a positive fit, at least in part, in any permitted swivel or angle positions of the swivel screw with respect to the bone plate using the segment of the conical male thread on the screw head of the clamping screw. In one embodiment the right-handed thread and/or the left-handed thread on the screw head may be embodied with multiple starts.

In one embodiment of the invention it may be provided that the male thread on the screw head of the clamping screw is a conical male thread that tapers on the screw head in the screw-in direction. This embodiment supports clamping screwing-in into the female thread, the clamping effect being optimized with a cylindrical female thread in particular.

One refinement of the invention can provide that for the clamping screw the conical male thread on the screw head is formed with a thread pitch that is smaller than the thread pitch on the shaft of the clamping screw. In one embodiment the thread pitches are embodied such that the conical male thread on the screw head is a fine-pitch thread and the bone thread on the shaft of the clamping screw is a coarse-pitch screw.

One advantageous embodiment of the invention provides that a hole transition with a through-passage is provided between the swivel hole and the clamping hole that is associated with the swivel hole. In one embodiment a type of longitudinal hole with a selectively narrow transition area can be formed in this manner.

Preferably a further embodiment of the invention provides that the bone plate is formed with an expansion area adjacent to the clamping hole such that the when the clamping screw is screwed into the female thread of the clamping hole the bone plate expands, at least somewhat, from the screw-in pressure due to the interaction between the male thread and the female thread and is deformable free of plastic deformation. In this manner, when the male thread of the screw head is screwed into the female thread, areas of the clamping hole can deform, not plastically, especially elastically, such that the clamping hole adapts to the form of the screw head and the screw is prevented from unscrewing by itself due to the peripheral stress. The embodiment providing the expansion area is preferably embodied such that the male thread is formed as a conical male thread and the female thread is embodied as a cylindrical female thread.

The clamping screw can be selectively screwed completely into the through-hole with the screw head. The screw head is held rotation-fast in each position by the elastic tension, but on the other hand the bone plate is also not irreversibly deformed in its plastic area, i.e. it is not overstretched. What can be achieved in this manner is that the clamping screw can be screwed in precisely, using sensitivity, until it is necessary to fix the bone plate securely against the bone and to attain clamping with the swivel screw, it being possible at the same time to ensure that the screw head in its most raised areas does not project over the bone plate, either, so that the fixed bone plate overall, with the clamping screw, essentially forms a smoothly molded unit on the bone without raised areas. In one embodiment it can be provided that the adjacent expansion area is embodied at least in part as a rib or a part of a ring.

In one useful embodiment of the invention it can be provided that for the clamping screw the length of the screw shaft is the same as or shorter than the length of the screw shaft of the swivel screw. In one embodiment the length of the shaft of the clamping screw is at most half the length of the shaft of the swivel screw, preferably at most one-third the length of the shaft of the swivel screw. The abbreviated length of the shaft of the clamping screw compared to the shaft of the swivel screw especially supports the diversity of the swivel or angle positions of the swivel screw with respect to the bone plate. Thus in one embodiment the shaft of the swivel screw can also be swiveled in an area below the lower shaft end of the clamping screw.

One advantageous embodiment of the invention provides that for the clamping screw a bone thread is formed on the screw shaft adjacent to the screw head with an expanding segment and is formed on the transition area essentially connecting to the thread base of the conical male thread.

One further embodiment of the invention provides that formed in the bone plate is at least one additional through-hole that is embodied according to the swivel hole or the clamping hole and that corresponds to the swivel hole and to the clamping hole, in that introduced into the additional through-hole is an additional bone screw that is embodied according to the swivel screw or the clamping screw, and in that the screw head of the additional bone screw when screwed in is locked up with the screw heads, for instance the spherical head and the screw head with the conical male thread, and the bone plate. In this embodiment an arrangement of at least three through-holes associated with one another is formed, into each of which a bone screw is screwed in. Any desired combinations of swivel screws and clamping screws may be provided, thread segments of the screw heads for the bone screws used selectively meshing in a positive fit by pair and thus supporting one another and being secured on the bone plate against a relative movement.

Preferred embodiments of the invention shall be explained in greater detail in the following.

The swivel hole and the associated clamping hole may be part of a so-called plate-hole group with additional through-holes or may form them. The bone plate may have a plurality of plate hole groups. Additional through-holes may be shaped as round or longitudinal holes for custom-fit receiving of round head, countersunk head, spherical head, oval head, or conical head screws. One swivel screw that is particularly advantageous for the bone plate has a spherical screw head that is flattened at the end of the head (north pole).

One preferred clamping screw is embodied as a countersunk head screw having a cylindrical thread below the countersunk head. The shape of the lower surface of the countersunk head screw may be rounded for improving the contact surface and fitting to the spherical shape of the swivel screw head. The length of the cylindrical thread of the screw bolt is a multiple of the plate thickness, for instance 0.9 times the plate thickness. Because of this the cylindrical thread of the clamping screw can initially securely bite into the cylindrical counterthread of the plate and in the further course of the screwing-in press the swivel screw against its planned location so that a clamping effect that is as great as possible is provided. This is particularly advantageous for slightly canted swivel screws. During the process of locking up, the cylinder thread of the clamping screw projects slightly over the bone plate lower surface, which is why the beginning of the screw tip-side cylinder thread can be embodied as a tapping thread, so that the cylinder thread can penetrate slightly into the bones to be screwed. The other, as a rule longer, screw tip-side part of the bolt of the clamping screw is typically embodied like a bone screw with a tapping thread.

The male thread of the clamping screw, which is intended to bite in the counterthread of the bone plate, may be embodied as a conical thread, the angle of inclination of the cone to the longitudinal axis of the screw being smaller than the angle of inclination of the countersunk head.

When used, first the swivel screw may be screwed in polyaxially, which makes it possible to fix bone fragments and to draw them to the plate. Then the clamping screw can screwed in and simultaneously fix itself and the swivel screw at a fixed angle during the final rotations. The clamping screw itself acts as a monoaxial fixed-angle screw.

In one embodiment, the polyaxial aspect of the swivel screw is limited by the outer edge of the screw bolt of the swivel screw, this outer edge when swiveled striking the lower edge of the swivel hole of the plate (corresponds to the bone plate side facing away from the screw head). In order to attain a high variable adjustment of the swivel screw longitudinal axis, the bolt is preferably released in the area below the screw head by a thread. The lower side of the swivel hole preferably also has a bevel in order to expand a swivel radius of the swivel screw. Because of this the screw longitudinal axis can be inserted variable to the hole axis up to a greatest possible azimuth angle.

In order to prevent the conical thread of the clamping screw from being destroyed by friction on the spherical head of the swivel screw, the thread may advantageously have rounded tips.

In another exemplary embodiment, the surface of the swivel screw is embodied such that the round head surface of the swivel screw has longitudinal segments, for instance 12 longitudinal segments, perpendicular to the equator of the screw head. Each longitudinal segment is configured with one sharp V female threaded column in order to act as a positive fit counterbearing for the clamping screw. With this it is possible to have fixed-angle positive fit fixation of both screws as follows. The clamping screw has a conical sharp V male thread that itself permits locking up with the plate via a conical sharp V female thread in the clamping hole. The swivel screw is fixed in a positive fit via its inner threaded columns to the screw head. The inner threaded columns on the swivel screw are embodied for instance such that the surface of the screw head part of the swivel screw still has sufficient spherical surface so that when the swivel screw is tightened the thread is not destroyed and no burrs are formed.

In another advantageous embodiment the surface of the swivel hole may be configured with at least one sharp V female threaded column in order to provide higher angular stability during assembly. Since the swivel screw may also be configured with preferably 12 inner threaded columns, the aforesaid sharp V female threaded columns on the surface of the swivel hole may advantageously be embodied with an adapted or fittable thread shape.

Using such inner threaded columns embodied on surfaces of swivel holes attains increased angular stability. This can be advantageous in bone plate systems for treating for instance fractures of the femur. One obvious disadvantage of the inner threaded columns in the surface of the swivel hole is a limited opportunity to draw bone fragments with the swivel screw, which is a consequence of the positive fit between the swivel screw and the aforesaid inner threaded columns. This disadvantage, that is, a limited opportunity to draw fragments, can also be used clinically as an advantage in an embodiment in that a certain angular stability is attained after inserting just a swivel screw. A higher and more robust angular stability of the swivel screw is attained with the clamping screw once a clamping screw has been inserted.

By varying the surface of the swivel hole, whether with or without at least one sharp V female threaded column, it is also possible to predetermine the amount of angular stability of the swivel screw, which permits advantageous adaptation to clinical requirements.

The suggested bone plate system in its various embodiments attains various advantages over conventional implants. These are for instance one or more of the following advantages:

Improved hold of a pair of divergent fixed-angle bone screws (or a plurality of fixed-angle screws) compared to one fixed-angle screw.

Due to improved hold of the bone screws it is possible to use shorter or narrower bone plates.

Due to improved hold of the bone screws the new system is particularly suitable for osteosynthesis of osteoporotic bones.

More fixed-angle screws can be added in a small space at plate ends.

In a short embodiment the clamping screw can simply lock up, or in a longer embodiment it can also be used as a monoaxial fixed-angle screw.

Improved use in periprosthetic fractures.

The swivel screw can draw bone fragments and then be fixed at a fixed angle by the clamping screw.

DESCRIPTION OF PREFERRED EXEMPLARY EMBODIMENTS OF THE INVENTION

The invention shall be described in greater detail in the following using preferred exemplary embodiments, referring to figures.

FIG. 1b is a longitudinal section through the swivel screw from FIG. 1a;

FIG. 1c is a longitudinal section through the clamping screw from FIG. 1a;

FIG. 2b is a longitudinal section through the swivel screw from FIG. 2a;

FIG. 2c is a longitudinal section through the clamping screw from FIG. 2a;

FIG. 3a is a top view onto a bone plate having a plate hole group;

FIG. 3b is a top view onto a bone plate having a plate hole group in accordance with a further embodiment;

FIG. 3c is a modification of the bone plate from FIG. 3b;

FIG. 4a is a longitudinal section through a swivel screw having a flattened spherical head and having inner threaded columns on the spherical head surface;

FIG. 4b is a top view onto the swivel screw from FIG. 4a;

FIG. 6a is a bone plate system having a suitable swivel screw and the clamping screw from FIG. 5c;

FIG. 6b is a section through the clamping hole from FIG. 6a along the line A-B from FIG. 6a for receiving a clamping screw from FIGS. 5b and 5c;

FIG. 7a is a top view onto a bone plate having a plate hole group;

FIG. 7b is a modification of the embodiment in FIG. 7a having a modified plate hole group;

FIG. 10 is a schematic depiction of a segment of another bone plate system, a clamping screw having a conical male thread on the screw head being partially screwed into a cylindrical female thread;

Figure 1A:
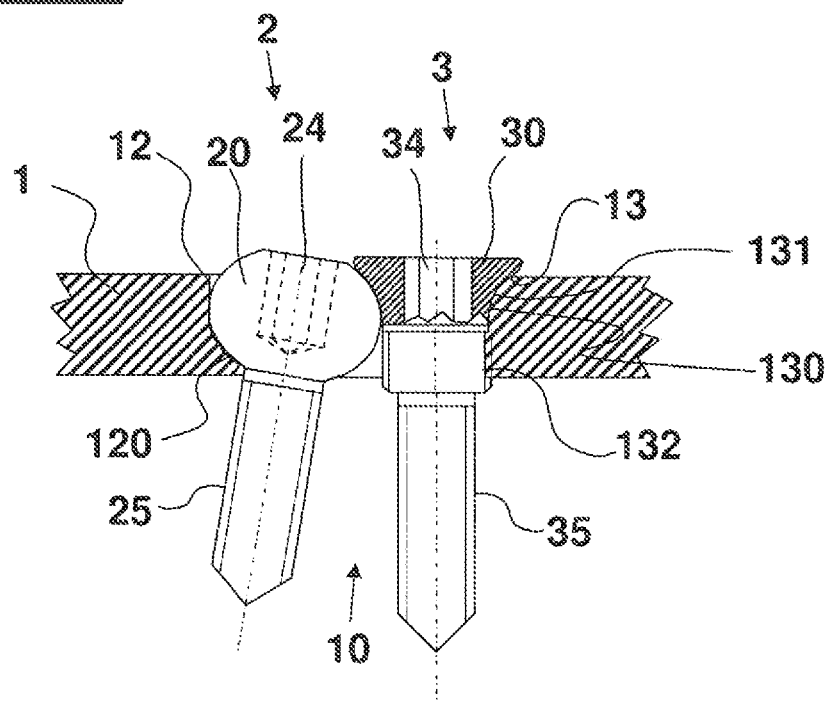
FIG. 1a is a longitudinal section through a bone plate system having a bone plate, a swivel screw, and a clamping screw.

FIG. 1a is a schematic partial section through a bone plate 1 having a plate hole group 10 with a swivel hole 12 and a clamping hole 13 that are arranged at a pre-specified distance from one another, a swivel screw 2 being arranged in the swivel hole 12 and a clamping screw 3 being arranged in the clamping hole 13. In an area of the bone plate 1 facing a bone the swivel hole 12 includes a tapering 120 that is selectively embodied in a positive fit with the screw head 20 of the swivel screw 2, and the clamping hole 13 includes a tapering 130 that is selectively embodied in a positive fit with the screw head 30 of the clamping screw 3.

Figure 1B:
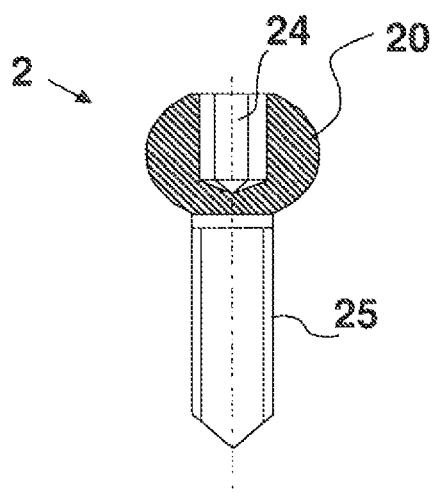

In the embodiment in FIG. 1a, the swivel screw 2 includes a spherically embodied screw head 20 that is flattened and in addition a hexagonal socket 24 for rotating the screw with a suitable tool. The swivel screw 2 depicted in FIG. 1b without the bone plate 1 has a thread for a bone screw 25.

In the embodiment in FIG. 1a, embodied in the area of the side of the bone plate 1 of the clamping hole 13 that faces away from a bone is a curved countersunk hole 131 that corresponds to and is shaped to fit a curved countersunk head 31 of the screw head 30 of the clamping screw 3, the clamping hole 13 adjacent to the tapering 130 of the clamping hole 13 being cylindrically embodied and a cylindrical sharp V female thread 132 being embodied in the cylindrically embodied area of the clamping hole and corresponding to a cylindrical sharp V male thread 32 of the clamping screw 3 that connects to the screw head 30 of the clamping screw 3.

Figure 1C:
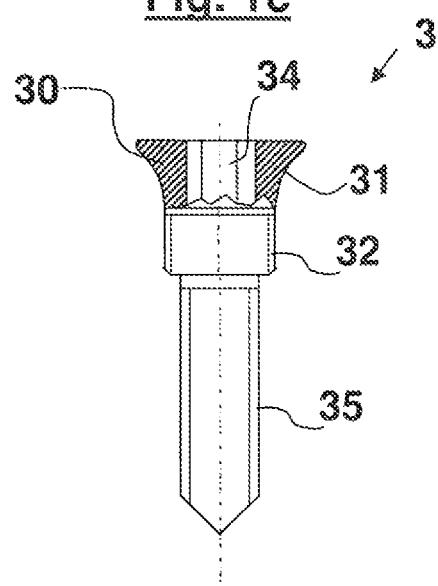

FIG. 1c provides a schematic depiction of the clamping screw 3 without the bone plate 1 with the screw head 30, the curved countersunk head 31 of the screw head 30, and the cylindrical sharp V male thread 32, the clamping screw 3 also having in its screw head 30 a hexagonal socket 34 and including a thread for a bone screw 35.

In the embodiment in FIG. 1 the screw head 30 for the clamping screw 3 is embodied to have a positive fit with the screw head 20 of the swivel screw 2 and consequently the clamping hole 13 with the correspondingly embodied tapering 130 is also embodied to have a positive fit with the screw head 30 of the clamping screw 3.

The embodiment in FIG. 1 of the bone plate 1, the plate hole group 10, and the swivel hole 12 and the clamping hole 13 and the swivel screw 2 and the clamping screw 3 is particularly advantageous since due to the positive fit embodiment of the screw head 20 of the swivel screw 2 with the swivel hole 12 and with the screw head 30 of the clamping screw 3 and in addition due to the positive fit embodiment of the screw head 30 of the clamping screw 3 with the clamping hole 13 a particularly stable and durable locking up of bone plate 1, swivel screw 2, and clamping screw 3 is made possible.

Figure 2A:
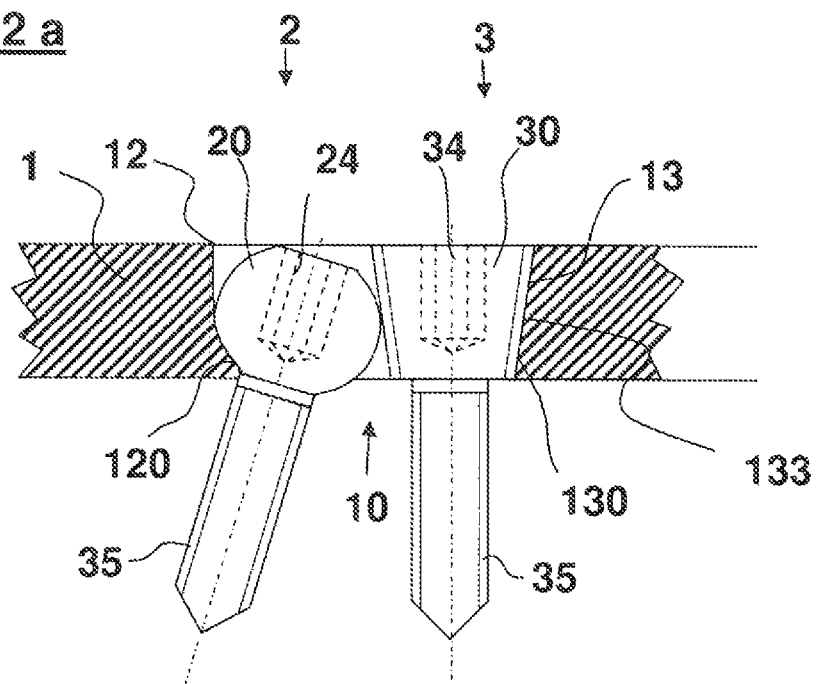
FIG. 2a is a longitudinal section through a bone plate system having a bone plate, a swivel screw, and a clamping screw in accordance with a further embodiment.
Figure 2B:
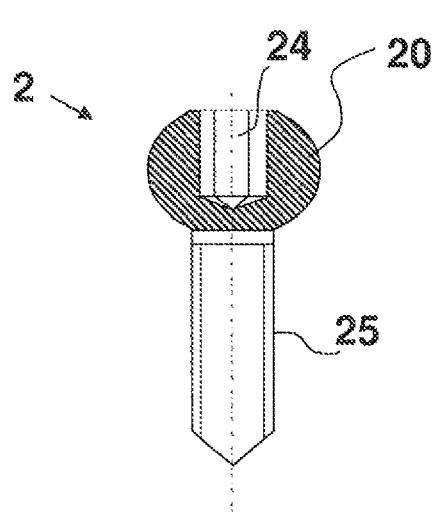
Figure 2C:
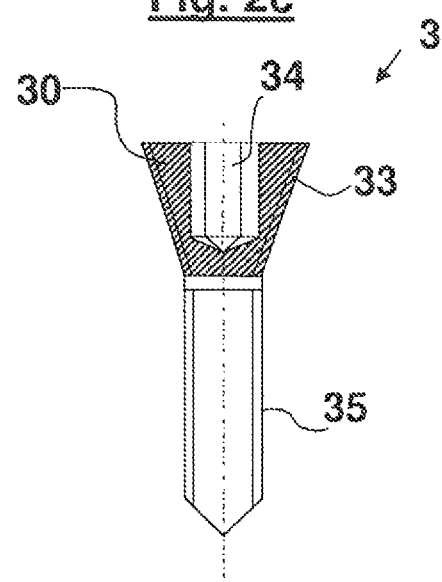

FIG. 2a is a modification of the bone plate 1 from FIG. 1a having the swivel screw 2 and clamping screw 3, and FIGS. 2b and 2c respectively depict the swivel screw 2 and the clamping screw 3 from FIG. 2a.

The embodiment of the bone plate 1 in FIG. 2a is embodied similar to the bone plate 1 in FIG. 1a, the same reference numbers being used for identical and similar embodiments, and reference is made to the foregoing description of FIG. 1 for identical embodiments. The same is true for embodiments of the swivel screw 2 and the clamping screw 3.

In contrast to the embodiment of the bone plate 1 in FIG. 1, in the embodiment in FIG. 2 the tapering 130 of the clamping hole 3 is continuously conical and embodied in the conically embodied area of the clamping hole 13 is a sharp V female thread 133 that corresponds to the sharp V male thread 33 that is on the clamping screw 3 and that is embodied on a conically embodied countersunk head 30 of the clamping screw 3 that corresponds to the conically embodied clamping hole 13.

In the embodiment in FIG. 2, the bone plate 1 also has a thickness compared to the screw heads 20 and 30 of the swivel screw 2 and of the clamping screw 3, so that the screw heads 20 and 30 of the screws 2 and 3 can each be completely countersunk into their respective holes 12 and 13 of the plate hole group 10, which advantageously provides a top side for the bone plate 1 without elevations from the screw heads 20 and 30.

The embodiments in FIGS. 1 and 2 have in common that a distance between the holes 12 and 13 and the dimension of the plate hole group 10 and the dimensions of the screw heads 20 and 30 are selected in advance such that when the screws 2 and 3 are completely screwed into the bone plate 1 a fixed-angle clamping effect is provided between the screws 20 and 30 and between the screws 20 and 30 and the bone plate 1. A combination of the embodiments in FIGS. 1 and 2 may also be provided, for instance a bone plate 1 from FIG. 1a that is embodied thicker so that the screw heads 20 and 30 from the embodiment in FIG. 1 may be completely countersunk into the plate hole group 10.

FIGS. 3a, b, and c each provide a schematic top view onto a segment of a bone plate 1 having a plate hole group 10 with a swivel hole 12 for a swivel screw 2 and having a clamping hole 13 for a clamping screw 3, the swivel hole 12 and the clamping hole 13 being embodied at least partly intermeshing, the swivel hole 12 and the clamping hole 13 also being arranged at a pre-specified distance A from one another so that when the screws 2 and 3 are completely rotated into the holes 12 and 13 the screw heads 20 and 30 of the screws 2 and 3 lock up with one another and with the edges of the holes 12 and 13 of the bone plate 1 and fixed-angle fixation of the swivel screw 2 and the clamping screw 3 is provided.

As described in the foregoing using FIGS. 1 and 2, the holes 12 and 13 include in the area of the bone plate facing a bone taperings 120 and 130 that are suitably embodied corresponding to the respective screw heads 20 and 30, and wherein a curved countersunk hole 131 and a cylindrical sharp V female thread 130 or a conical sharp V female thread 133 may be embodied on the clamping hole 13.

In accordance with the invention, the holes 12 and 13 intermesh with one another at least in a first area of the bone plate that is facing away from a bone, wherein the holes 12 and 13 may be spaced apart from one another in the area facing a bone, as is depicted schematically in the embodiment in FIG. 3a.

FIG. 3b depicts a modification of the bone plate 1 from FIG. 3a in which the plate hole group 10 is advantageously embodied such that the intermeshing screw holes 12 and 13 form a contiguous through-hole. FIG. 3c depicts a particularly advantageous modification of the embodiment in FIG. 3b in which sharp V female threaded columns 121 are embodied in the swivel hole 12 that support a positive and/or non-positive fit and the screw head 20 of the swivel screw 2 locks up with the bone plate 1.

For further promoting the static friction and the screw head 20 of the swivel screw 2 locking up with the bone plate 1, in addition sharp V female threaded columns 21 may be embodied on the surface of the screw head 20 of the swivel head screw 2 that are also advantageously embodied corresponding to the sharp V female threaded columns 121 of the embodiment of the bone plate 1 in FIG. 3c.

FIG. 4a provides a schematic depiction of a screw head 20 of a swivel screw 2 having sharp V female threaded columns 21. FIG. 4b depicts the screw head 20 in FIG. 4a from above.

Naturally the screw head 20 provided with the sharp V threaded columns in the embodiment of the swivel screw 2 in FIG. 4 also promotes static friction and clamping with the bone plate 1 in FIG. 1, FIG. 2, FIGS. 3a and 3b, and with the clamping screw 3 in FIG. 1 and FIG. 2.

Figure 5:
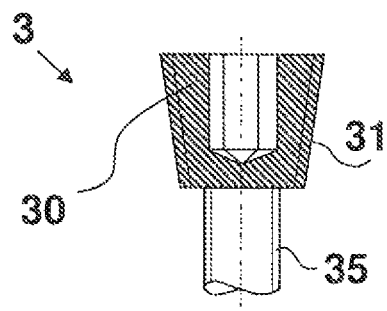
FIG. 5a is a longitudinal section through a clamping screw having a conical countersunk head and sharp V male thread.
FIG. 5b is a longitudinal section through a clamping screw having a cylindrical male thread and countersunk head with a conical lower surface of the countersunk head.
FIG. 5c is a longitudinal section through a clamping screw having a cylindrical male thread and countersunk head with radial ribs on the lower surface of the countersunk head.
Figure 5:
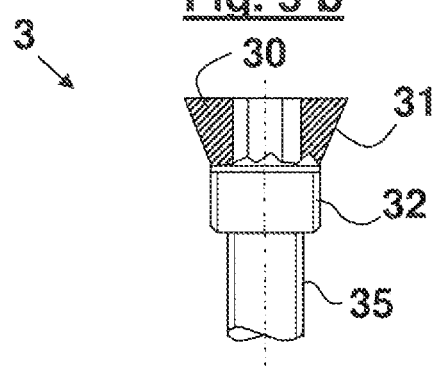
Figure 5:
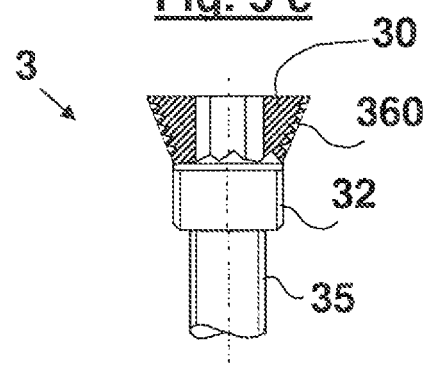

FIG. 5a is a partial schematic depiction of a clamping screw 3 that is particularly suitable for a bone plate 1 and that has the screw head 30 and a sharp V male thread 33 embodied on the screw head 30, the screw head 30 being embodied completely conical and being particularly suitable for a bone plate 1 from FIG. 2a. FIG. 5b is a partial schematic depiction of a screw 3 having the screw head 30 that is embodied conically 36 in a first area, to which is attached a cylindrically embodied area having a cylindrical sharp V male thread 32, the clamping screw 3 in FIG. 5b being particularly suitable for a combination (not shown in the drawings) of a bone plate 1 according to FIG. 1a and FIG. 2a with a clamping hole 13 that in a first area is embodied conically and in an area adjacent thereto is embodied cylindrically, the cylindrical area of the clamping hole 13 being provided with a corresponding sharp V female thread 32.

FIG. 5c is a schematic depiction of a modification of the clamping screw 3 in FIG. 5b, in which the screw head of the clamping screw 3 is embodied conically in a first 15 area and in a second adjacent area is embodied cylindrically, a cylindrical sharp V male thread 32 being embodied in the cylindrically embodied area. In contrast to the clamping screw 3 in FIG. 5b, the clamping screw 3 in FIG. 5c includes on its conically embodied head 30, instead of the conical surface of the countersunk head 20 of the clamping screw 3 in FIG. 5b, external radial ribs 360 that provide particularly good static friction and clamping between the screw head 30 of the clamping screw 3, with the bone plate 1, and the screw head 20 of the swivel screw 2. The countersunk head may be provided with a conical male thread instead of the radial external ribs 360.

FIG. 6a is a partial schematic depiction of a bone plate 1 according to another embodiment that is particularly suitable for fixing screws 3 according to FIG. 5c, wherein the clamping hole 13 in the bone plate 1 in FIG. 6a is conically embodied in a first area and in its conically embodied area can be provided without a thread 136 or with a sharp V female thread. In a second area adjacent to the first area, the clamping hole 13 is embodied cylindrically and provided with a cylindrical sharp V female thread 132 that corresponds to the cylindrical sharp V male thread 32 of the clamping screw 3 in FIG. 5c, the height of the cylindrical area of the clamping hole 13 provided with the female thread 132 in FIG. 6b in the bone plate 1 advantageously being less than the height of the cylindrical area of the clamping screw 3 provided with the male thread 32 in FIG. 5c so that the cylindrical area of the clamping screw 3 when the clamping screw 3 is completely rotated into the bone plate 1 projects by a pre-specified amount beyond the side of the bone plate 1 facing a bone as depicted in FIG. 6a, FIG. 6b also depicts a section through the bone plate 1 along the line A-B in FIG. 6a.

FIG. 7a is a schematic top view onto a bone plate 1 in accordance with another embodiment having a plate hole group 10 that includes two swivel holes 12 for swivel screws and also includes a clamping hole 13 for a clamping screw 3. The holes 12 and 13 are each embodied mutually intermeshing and are arranged at a pre-specified distance A. In the embodiment in FIG. 7a, the plate hole group 10 is embodied for instance and advantageously such that the intermeshing screw holes 12 and 13 form one contiguous through-hole.

As in the embodiment according to FIGS. 1, 2, and 6 described in the foregoing, in the embodiment in FIG. 7a the distance A between clamping hole 13 and swivel hole 12 is selected such that when the screws 2 and 3 are completely rotated into the holes 12 and 13 the screw heads 20 and 30 of the screws 2 and 3 lock up with one another and with the bone plate 1 so that fixed-angle fixation of swivel screw 2 and clamping screw 3 is provided. In the embodiment in FIG. 7a, the clamping hole 13 may be embodied in accordance with the embodiment from FIG. 1 or FIG. 2 or FIG. 6. The swivel hole 12 may be embodied in accordance with the swivel hole 12 from the embodiment in FIG. 3b or 3b, wherein the swivel hole may include sharp V female threaded columns 121, which is depicted schematically in the embodiment in FIG. 7b. One plate hole group 10 of a bone plate 1 may include a plurality of swivel holes 12 and/or clamping holes 13, each of which are embodied intermeshed with one another.

Figure 8:
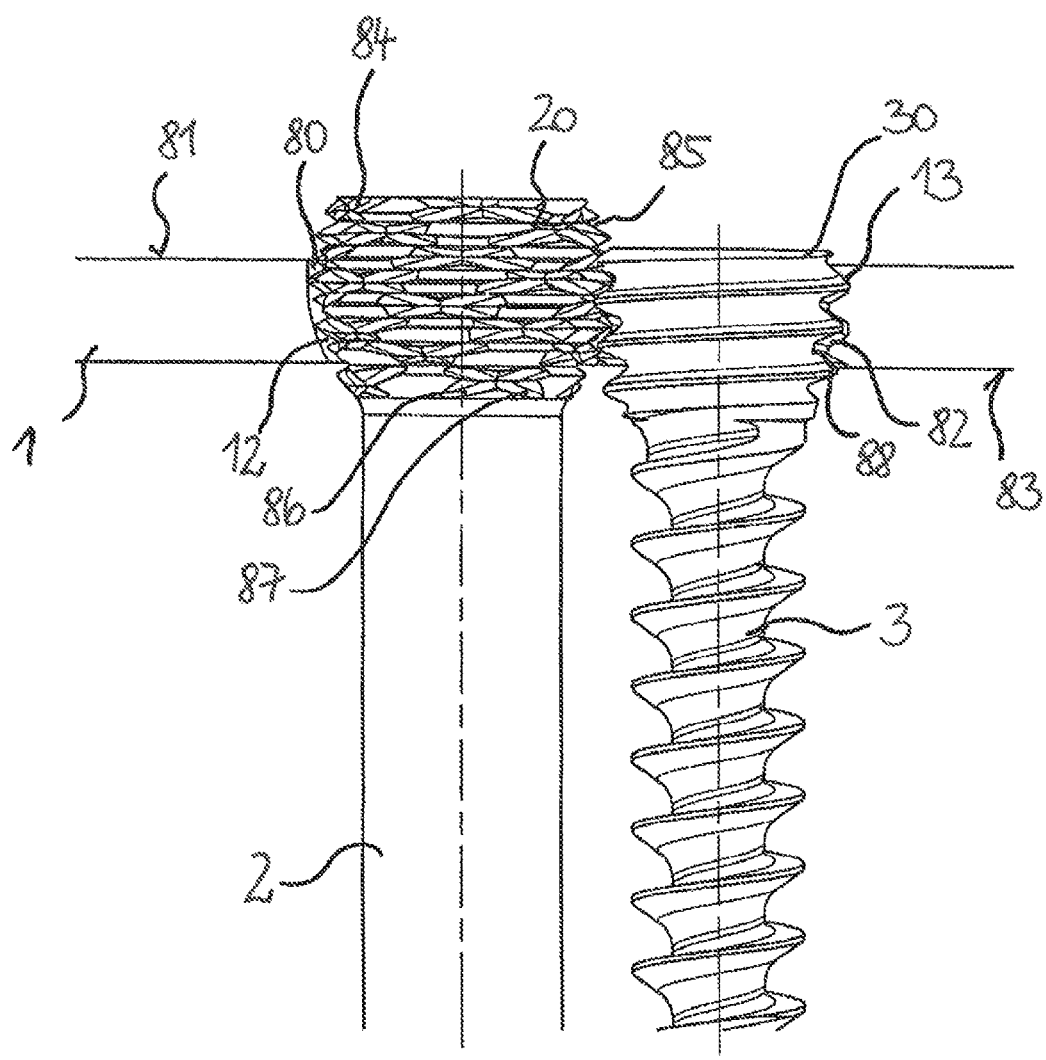
FIG. 8 is a schematic depiction of another bone plate system having a bone plate and bone screws fixed thereto in a fixed-angle manner according to another embodiment.

FIG. 8 provides a schematic depiction of a bone plate system having a bone plate 1 according to another embodiment, in which bone plate 1 the swivel hole 12 and the screw or clamping hole 13 associated with the swivel hole 12 are formed. The swivel hole 12 is produced with a spherical head seat 80 that opens to the top 81 of the bone plate 1. In the embodiment depicted the spherical head seat 80 is produced with an essentially smooth inner surface.

Similar to the cylindrical sharp V female thread 132, the screw or clamping hole 13 has a cylindrical female thread 82 that in the depicted embodiment extends across the entire height of the bone plate 1 from the top 81 to the bottom 83.

The swivel screw 2 embodied as bone screw is inserted into the swivel hole 12 such that the screw head 20 of the swivel screw 2 embodied as spherical head is disposed in the spherical head seat 80 essentially in a positive fit. The screw head 20 of the swivel screw 2, which may also be called a spherical head screw, is provided with a thread contour 84 that is formed with essentially horizontal circumferential grooves 85, a right-handed thread 86, and a left-handed thread 87. It can be provided that the right-handed and/or the left-handed thread 86, 87 are embodied with multiple starts.

Inserted into the screw or clamping hole 13 is the clamping screw 3, also embodied as a bone screw, which has on its screw head 30 a conical male thread 88 that is rotated into the cylindrical female thread 82 of the screw or clamping hole 13. Due to the cooperation between the cylindrical female thread 82 and the conical male thread 88, the clamping screw 3 is essentially fixed in its position relative to the bone plate 1, especially with respect to a spatial angular position to the bone plate 1.

Mutually opposing thread segments in the thread contour 84 and in the conical male thread 88 intermesh in a positive fit when screwed in as depicted in FIG. 1. When screwed in, the screw heads 20, 30 of the swivel screw 2 and the clamping screw 3 are locked up with one another and with the bone plate 1 so that they are fixed multidimensionally at a fixed angle.

Figure 9:
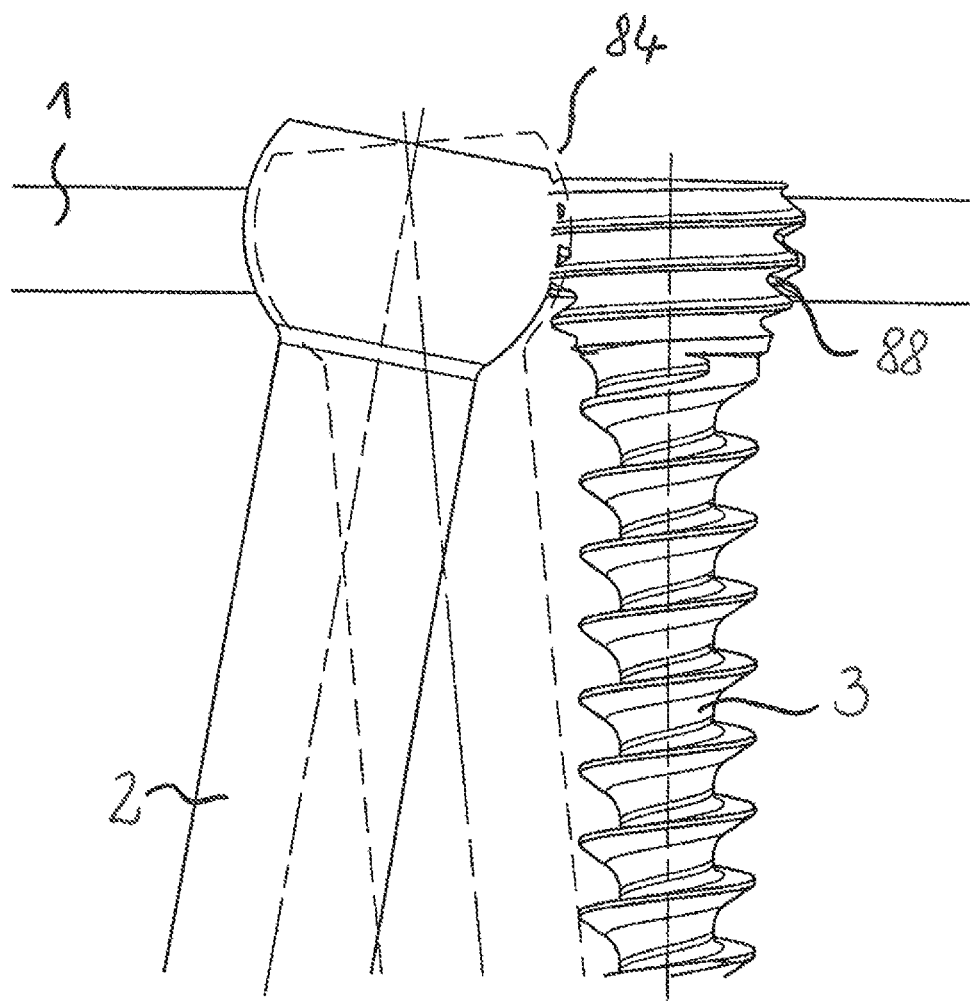
FIG. 9 is a schematic depiction of the bone plate system according to FIG. 8 with various swivel positions for a bone screw embodied as a swivel screw.
Figure 16:
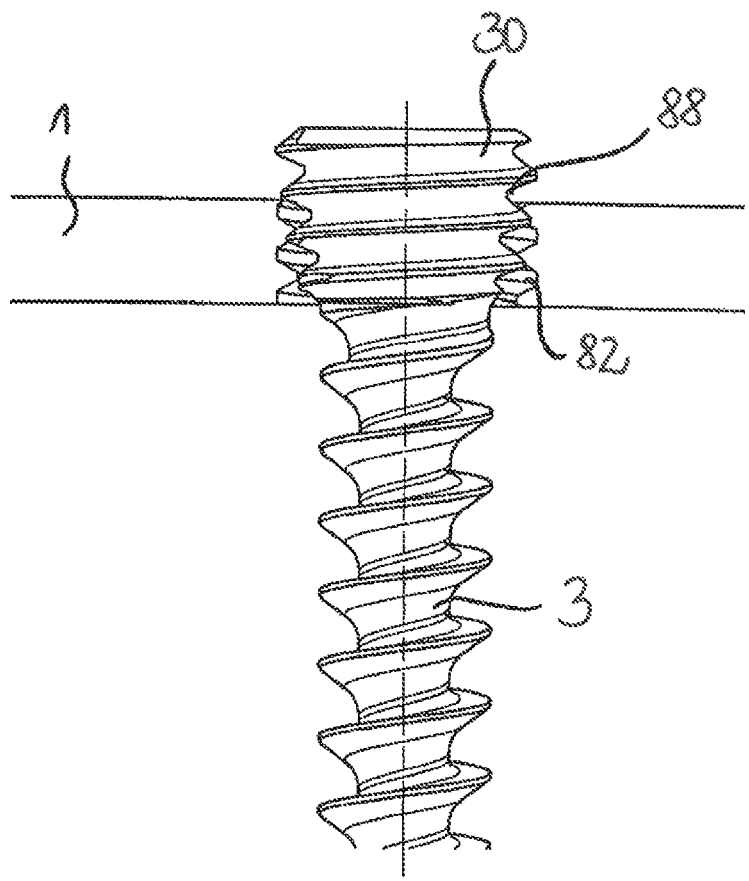

FIG. 9 is a schematic depiction of different angular or swivel positions of the swivel screw 2, thread segments of the thread contour 84 and of the conical male thread 88 intermeshing in a positive fit in each of the swivel positions (solid lines and broken lines).

FIG. 10 is a schematic depiction relating to the cooperation between the conical male thread 88 and the cylindrical female thread 82 when the clamping screw 3 is screwed in.

Figure 11:
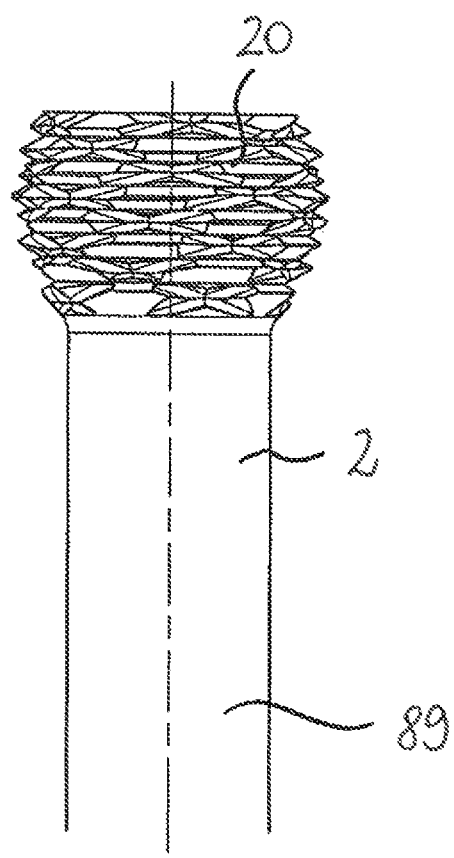
FIG. 11 is a schematic depiction of a bone screw embodied as a swivel screw and having a thread contour on the spherical screw head; and, FIG. 12 is a schematic depiction of a bone screw having a conical male thread on the screw head.

FIG. 11 is a schematic depiction of the swivel screw 2, the bone thread on the shaft 89 of the swivel screw 2 not being depicted as in FIGS. 1 and 2. It may be embodied for instance in the same manner as for the clamping screw 3 (see FIGS. 8 through 10).

Figure 12:
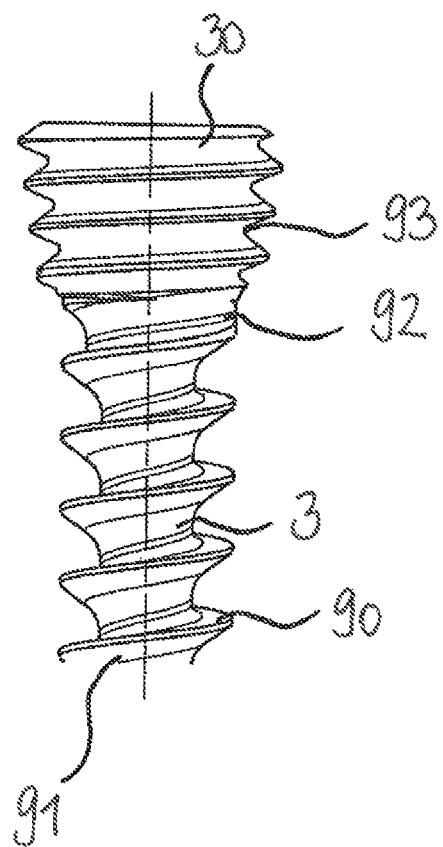

Finally, FIG. 12 is a schematic depiction of the clamping screw 3. Adjacent to the screw head 30, a bone thread 90 is formed on the shaft 91 of the clamping screw 3 with an expanding segment 92 and with an essentially connecting transition area at the thread base 93 of the conical male thread 88.

Additional mechanical modifications to the surfaces of swivel hole, swivel screw, clamping screw, and clamping hole may have a significant effect on static friction and/or positive fit between screws and/or between screw and bone plate. Among such mechanical modifications are:

Use of different implant materials such as pure titanium, titanium alloys, and other steel/metal implant alloys;

Different surface hardening of various components (for instance particular hardness for the fixing screw).

Radial thread or radial ribs of limited height on the surface of the swivel hole and/or on the surface of the clamping hole. Naturally one or a plurality of threads or ribs may be embodied in any other desired configurations.

Longitudinal thread or longitudinal ribs of limited height on the surface of the swivel screw and/or on the surface of the fixing screw. Naturally one or a plurality of threads or ribs may be embodied in any other desired configurations.

Surface roughness of the swivel hole and/or of the clamping hole and/or of the swivel screw head and/or of the fixing screw countersunk head (for instance by sandblasting).

Soft surface of the round head of the swivel screw (so that a harder thread for the cone of the clamping screw can bite into the softer spherical head).

Covering of the spherical head of the swivel screw with a biocompatible non-metallic material (especially polypropylene) or a transition metal (for instance tantalum). It is clear that resorbable biocompatible materials may also be used for the covering of the spherical head (for instance lactide). Due to the spherical head of the swivel screw being covered, a thread on the fixing screw head can dig into the softer covering on the swivel screw head. The biocompatible material should have a rough and low-wear surface.

Modified thread shapes such as for instance PG thread, NPT thread, trapezoidal thread, spherical thread.

Modified fixing screw geometry such as for instance embodiment as an oval head or pear-shaped head or modified screw head geometry like a concave or concave-like free shape for the head geometry in order to attain a positive fit with the head of the swivel screw.

Advantageous marking of the plates is also suggested in order to attain the most simple handling of the new plate-screw system possible during an operation. This is intended to achieve the most simple possible placement of the bone plate and addition of bone screws to screw holes. The identification or marking may be accomplished using engraving and/or printing and/or galvanically.

The bone plate system may also have one or a plurality of the following features in advantageous embodiments:

Anatomically molded plates in the joint areas for long bones, for instance the long bones in the extremities Balancing of materials in plate holes and plate hole groups in order to facilitate favorable bending in the area between holes No holes in plates in order to make it possible to fix the bone plate to the bones, for instance using wires, and (ii) to be able to fix threads or anchors to the bone plate.

Frequently bone plates can be inserted in a minimally invasive manner using target devices. In addition, specially embodied target devices are desirable in order to insert the plate-screw system for the suggested invention as safely as possible. The following features characterize inter alia a target device embodied advantageously for the bone plate system:

Target device with retention apparatus for the plate

Retention apparatus for the bone plate can be attached to the bone plate for instance using threads on sleeves that grip in one clamping hole or a plurality of clamping holes Target device includes one or a plurality of additional holes for wires for temporary plate fixation Target device is characterized by different markings for swivel screws and fixed screws. Marking may be produced for instance by engraving and/or printing.

One or a plurality of placeable jaws may be fixed on the target device for adding swivel holes. A placeable jaw is provided with an apparatus that can be used as a variably adjustable target apparatus for swivel screws. The target apparatus guides for instance a bushing (for receiving bore sleeves or sleeves for guiding screws) perpendicular to a curved surface of a spherical segment, the center point of the sphere coinciding or nearly coinciding with the center point of the swivel screw hole.

The bone plate may be used advantageously in fractures of the radius, humerus, femur, and tibia. In order to be able to have frequently used bore directions and screw lengths near joints, a plate attachment that provides favorable bore directions for swivel holes and clamping holes is desirable. Features of a plate attachment that is particularly suitable for this are:

The plate attachment has a thickness that is multiple times thicker than the bone plate (for instance three times thicker) and includes bores in directions that can typically or favorably be used in the respective joint regions.

The plate attachment includes markings for swivel holes and clamping holes.

The plate attachment can be provided with notations for common screw lengths. The notation can be applied for instance using engraving and/or printing.

The plate attachment includes one or a plurality of additional holes for wires for temporarily attaching the bone plate to the bone.

A clamping or screw mechanism permits rapid coupling of the plate attachment to the plate.

The features of the invention disclosed in the foregoing description, in the claims, and in the drawings may be significant, individually or in any desired combination, for the realization of the invention in its various embodiments.

The invention claimed is:

1. A bone plate system for osteosynthesis, comprising:
a bone plate having a top surface and a bottom surface,
a swivel screw having a spherical screw head,
a clamping screw having a threaded screw head,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone, and
wherein the swivel hole is defined in-part by a curved surface that defines a sphere, the curved surface extending continuously from the top surface of the bone plate to the bottom surface of the bone plate, the curved surface acting as a seat for the spherical screw head of the swivel screw which is shaped complementary to the seat, and the spherical screw head of the swivel screw is engaged with at least a lowermost portion of the seat and the threaded screw head of the clamping screw.

2. A bone plate system in accordance with claim 1, wherein the seat is formed at least with one of a smooth surface and with a surface roughness.

3. A bone plate system in accordance with claim 1, wherein the clamping hole has a female thread.

4. A bone plate system in accordance with claim 3, wherein the screw head of the clamping screw has a male thread.

5. A bone plate system in accordance with claim 4, wherein the bone plate is formed with an expansion area adjacent to the clamping hole such that when the clamping screw is screwed into the female thread of the clamping hole the bone plate expands.

6. A bone plate system in accordance with claim 4, wherein a bone thread is formed on a screw shaft of the clamping screw with a segment located between the screw shaft and the male thread of the screw head of the clamping screw.

7. A bone plate system in accordance with claim 4, wherein
the screw head of the swivel screw has a thread configuration that is formed with circumferential grooves, each groove lying in a respective plane which extends transverse to a longitudinal axis of the swivel screw,
the male thread of the screw head for the clamping screw when the clamping screw is screwed in is at least partially screwed into the female thread of the clamping hole, and
when screwed in, surface segments of the thread configuration on the screw head of the swivel screw and of the male thread on the screw head of the clamping screw mutually engage in a positive fit.

8. A bone plate system in accordance with claim 4, wherein the male thread on the screw head of the clamping screw is formed with a V-shape in a cross section transverse to a longitudinal axis of the clamping screw.

9. A bone plate system in accordance with claim 8, wherein the male thread is formed with a thread pitch that is smaller than a thread pitch on a screw shaft of the clamping screw.

10. A bone plate system in accordance with claim 1, wherein a through-passage is provided between the swivel hole and the clamping hole that is associated with the swivel hole.

11. A bone plate system in accordance with claim 1, wherein a length of a screw shaft of the clamping screw is the same as or shorter than a length of a screw shaft of the swivel screw.

12. A bone plate system in accordance with claim 1, wherein
formed in the bone plate is at least one other additional through-hole that is configured similar in shape to the swivel hole or the clamping hole,
introduced into the other additional through-hole is an additional bone screw with a screw head that is configured similar in shape to the screw head of the swivel screw or the clamping screw, and
the screw head of the additional bone screw when screwed in, is secured with the screw heads of the swivel screw and the clamping screw as well as with the bone plate against a relative movement.

13. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone, and
wherein the screw head of the clamping screw has a male thread.

14. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone,
wherein the screw head of the clamping screw has a male thread, and
wherein
the screw head of the swivel screw has a thread configuration that is formed with circumferential grooves, each groove lying in a respective horizontal planes which extends transverse to a longitudinal axis of the swivel screw,
the male thread of the screw head for the clamping screw when the clamping screw is screwed in is at least partially screwed into the female thread of the clamping hole, and
when screwed in, surface segments of the thread configuration on the screw head of the swivel screw and of the male thread on the screw head of the clamping screw mutually engage in a positive fit.

15. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone,
wherein the screw head of the clamping screw has a male thread, and
wherein the male thread on the screw head of the clamping screw is formed with a V-shape in a cross section transverse to a longitudinal axis of the clamping screw.

16. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone,
wherein the screw head of the clamping screw has a male thread,
wherein the male thread on the screw head of the clamping screw is formed with a V-shape in a cross section transverse to a longitudinal axis of the clamping screw, and
wherein the male thread is formed with a thread pitch that is smaller than a thread pitch on a screw shaft of the clamping screw.

17. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone,
wherein the clamping hole has a female thread, and
wherein the bone plate is formed with an expansion area adjacent to the clamping hole such that when the clamping screw is screwed into the female thread of the clamping hole, the bone plate expands.

18. A bone plate system for osteosynthesis, comprising:
a bone plate,
a swivel screw,
a clamping screw,
a swivel hole that is formed in the bone plate as a through-hole for polyaxially receiving the swivel screw, and
a clamping hole that is associated with the swivel hole and that is formed in the bone plate as an additional through-hole for receiving the clamping screw,
wherein when screwed in, the swivel screw and the clamping screw are fixed at a fixed angle relative to one another in that screw heads of the swivel screw and the clamping screw are secured to one another and to the bone plate against a relative movement, and wherein the swivel screw and the clamping screw are each adapted to be screwed into a bone, wherein the screw head of the clamping screw has a male thread, and wherein a bone thread is formed on a screw shaft of the clamping screw with a segment located between the screw shaft and the male thread of the screw head of the clamping screw.

* * * * *

UNITED STATES PATENT AND TRADEMARK OFFICE
CERTIFICATE OF CORRECTION

PATENT NO. : 9,161,795 B2  
APPLICATION NO. : 13/517949  
DATED : October 20, 2015  
INVENTOR(S) : Bernhard Clasbrummel, Curt Kranz and Susanne Kahl It is certified that error appears in the above-identified patent and that said Letters Patent is hereby corrected as shown below:

In the Claims

In claim 14, at column 15, line 41, "planes" should instead read --plane--.

Signed and Sealed this  
Eighth Day of March, 2016

Michelle K. Lee  
*Director of the United States Patent and Trademark Office*